US008726903B2

(12) United States Patent
Levine

(10) Patent No.: US 8,726,903 B2
(45) Date of Patent: May 20, 2014

(54) RESPIRATORY FACEMASK WITH SLIDING ENDOTRACHEAL TUBE HOLDER

(76) Inventor: Walter Levine, Delray Beach, FL (US)

( * ) Notice: Subject to any disclaimer, the term of this patent is extended or adjusted under 35 U.S.C. 154(b) by 0 days.

(21) Appl. No.: 13/478,836

(22) Filed: May 23, 2012

(65) Prior Publication Data

US 2012/0227747 A1    Sep. 13, 2012

Related U.S. Application Data

(63) Continuation-in-part of application No. 12/956,627, filed on Nov. 30, 2010, now abandoned.

(60) Provisional application No. 61/265,138, filed on Nov. 30, 2009.

(51) Int. Cl.
*A61M 16/00*    (2006.01)
*A61M 5/32*    (2006.01)

(52) U.S. Cl.
USPC ..................... 128/207.14; 604/174; 604/178

(58) Field of Classification Search
USPC ..................... 128/207.14; 604/174, 178–179
See application file for complete search history.

(56) References Cited

U.S. PATENT DOCUMENTS

| 4,744,358 | A | * | 5/1988 | McGinnis ................. 128/207.17 |
| 5,271,586 | A | * | 12/1993 | Schmidt .......................... 248/58 |
| 5,345,931 | A | * | 9/1994 | Battaglia, Jr. ............. 128/207.17 |
| 5,479,921 | A | | 1/1996 | Reif |
| 5,735,002 | A | * | 4/1998 | Kistner ...................... 5/81.1 HS |
| 5,806,516 | A | * | 9/1998 | Beattie ..................... 128/207.17 |
| 6,067,985 | A | * | 5/2000 | Islava ....................... 128/207.17 |
| 6,076,991 | A | * | 6/2000 | Karlsen et al. ................ 403/381 |
| 6,474,332 | B2 | | 11/2002 | Arndt |
| 6,578,576 | B1 | * | 6/2003 | Taormina et al. ........ 128/207.17 |
| 7,275,536 | B2 | | 10/2007 | Godoy |
| 7,296,574 | B2 | | 11/2007 | Ho et al. |
| 2007/0142784 | A1 | * | 6/2007 | Dikeman et al. ............. 604/174 |
| 2007/0163596 | A1 | | 7/2007 | Mikkaichi et al. |
| 2008/0078031 | A1 | * | 4/2008 | Weinstein et al. ................ 5/630 |

* cited by examiner

*Primary Examiner* — Oren Ginsberg
*Assistant Examiner* — Jennifer M Deichl
(74) *Attorney, Agent, or Firm* — Greer, Burns & Crain, Ltd.

(57) ABSTRACT

A respiratory therapy facemask configured to be positioned against a patient's face and adjacent the patient's mouth, includes a face plate configured for attachment to the patient and defining an opening, the face plate including a laterally extending track defining a slot. A tube rest assembly is configured for being slidably engaged in the slot and for securely accommodating an endotracheal tube. The tube rest assembly is configured for directly engaging the track for lateral movement in the opening.

24 Claims, 13 Drawing Sheets

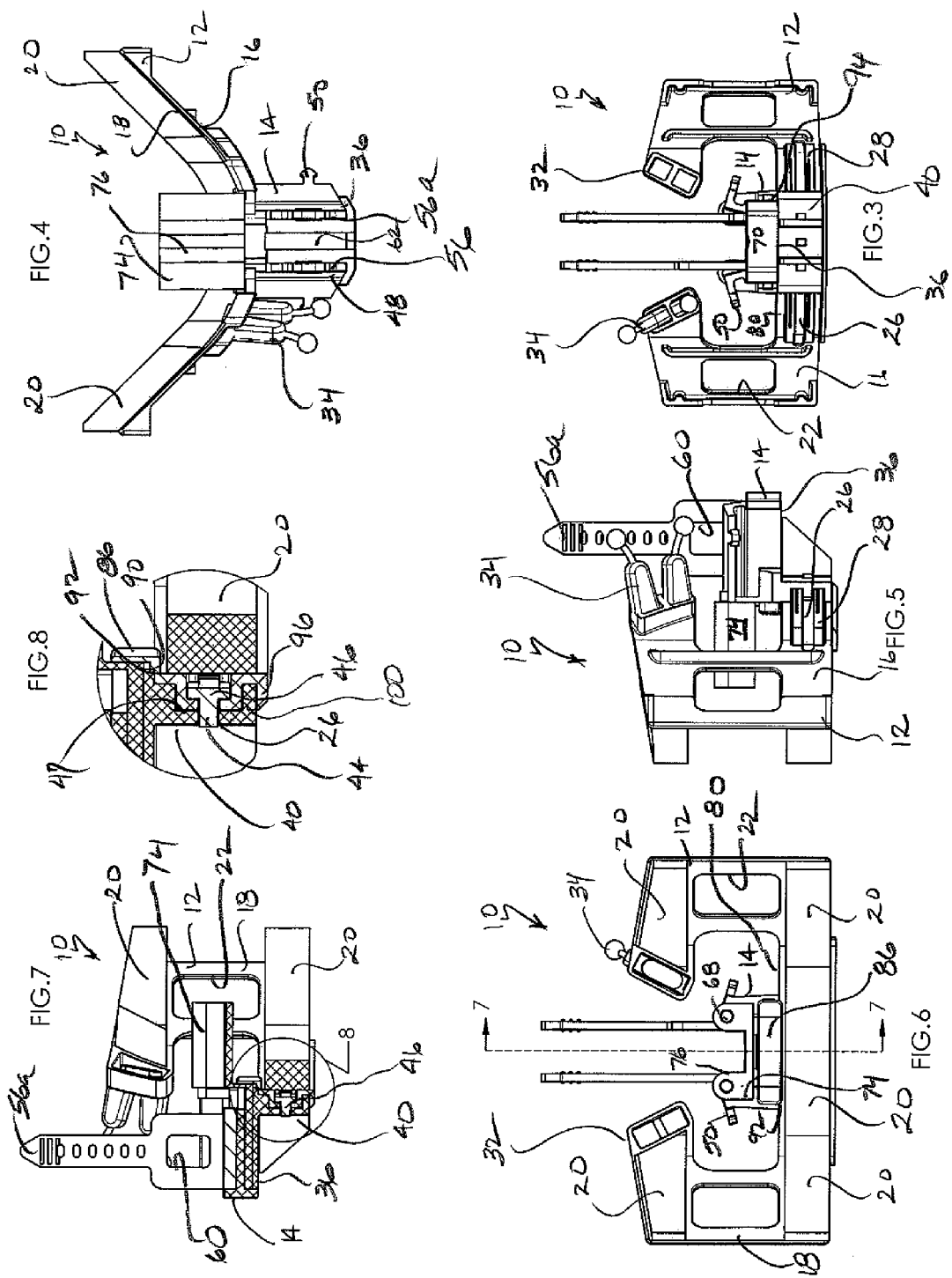

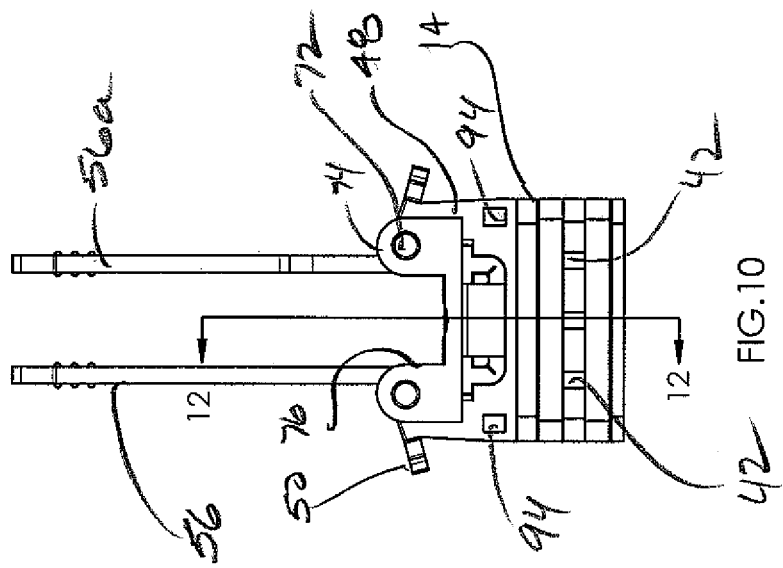
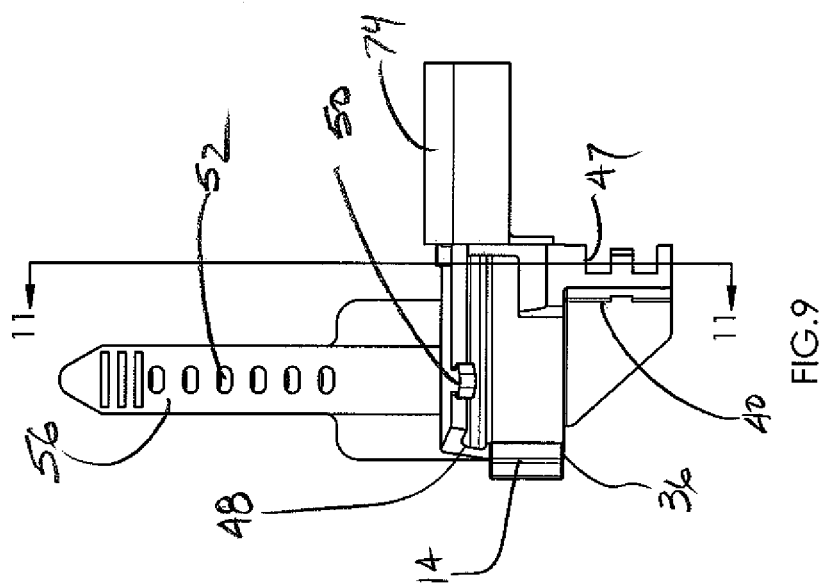

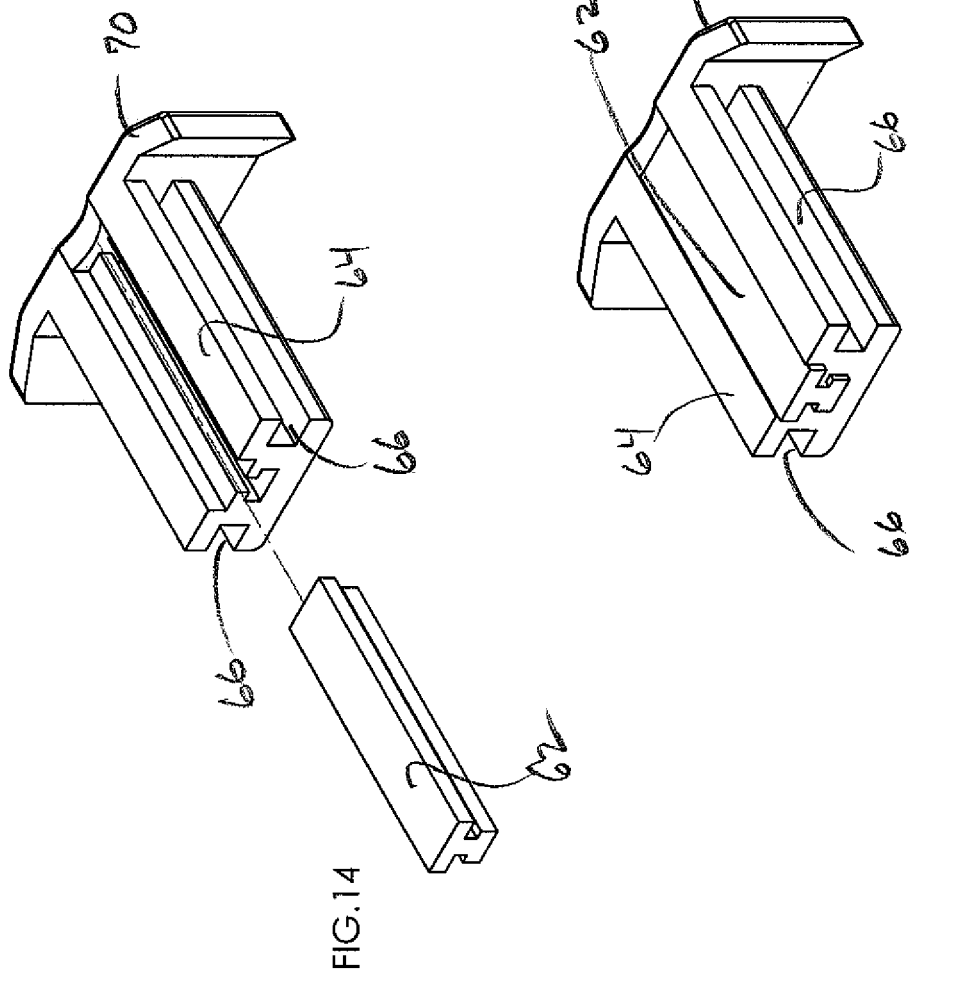

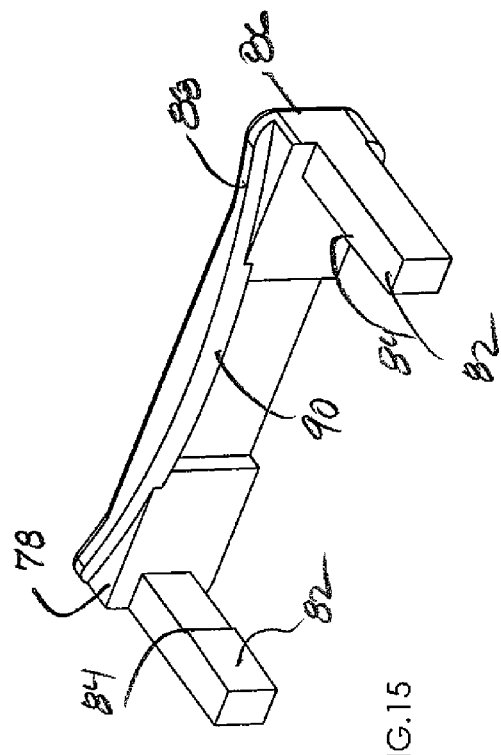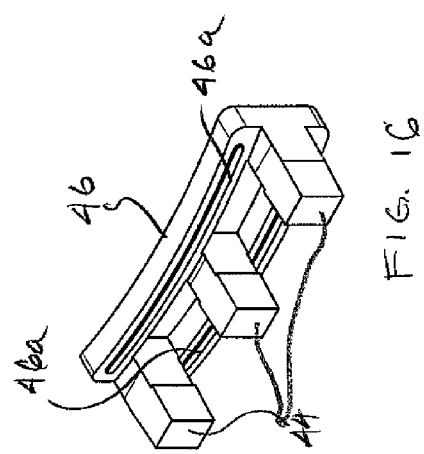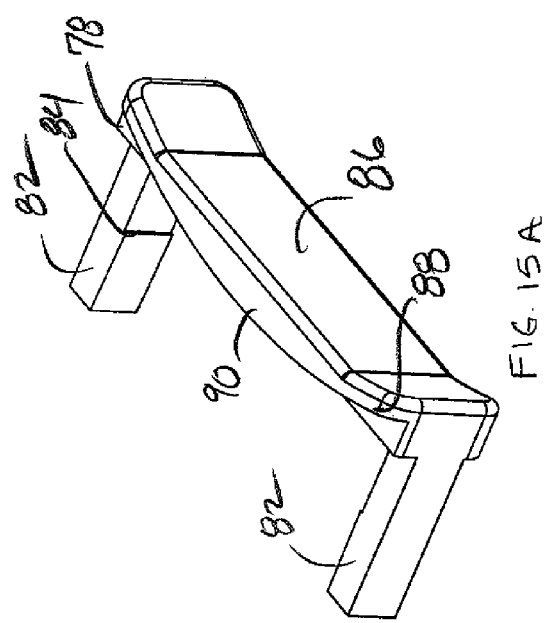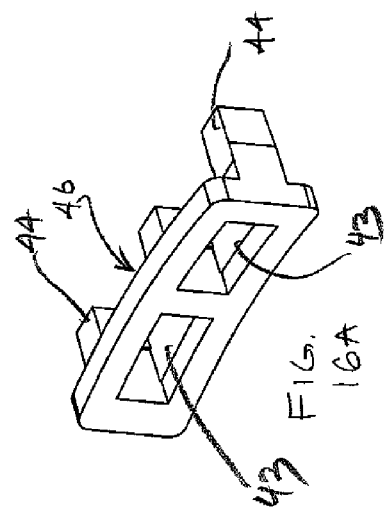

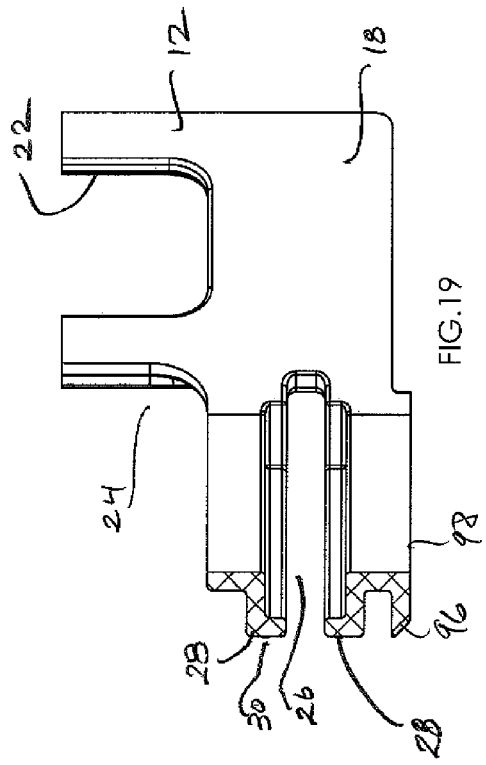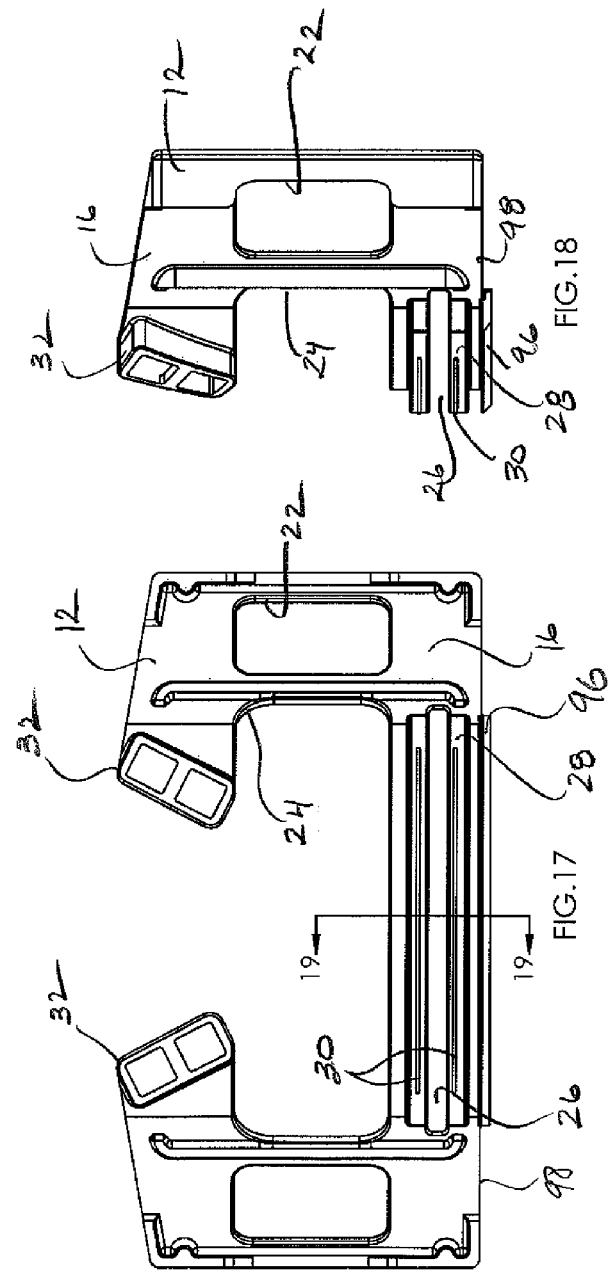

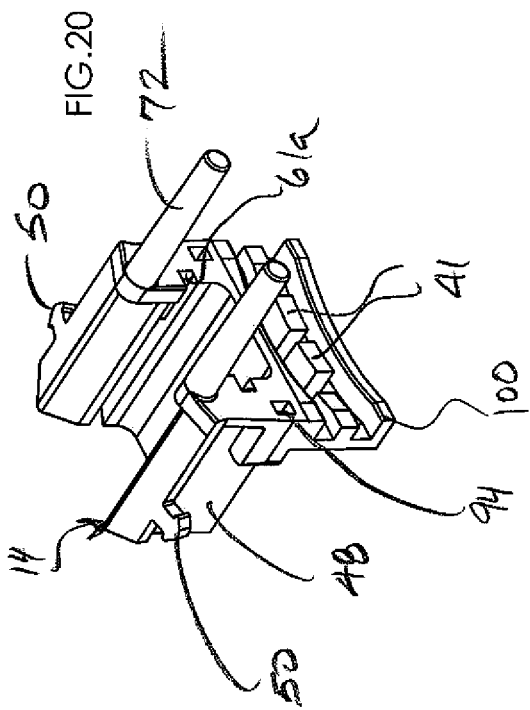
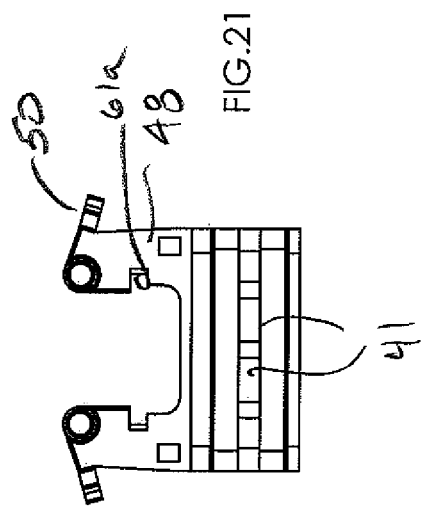
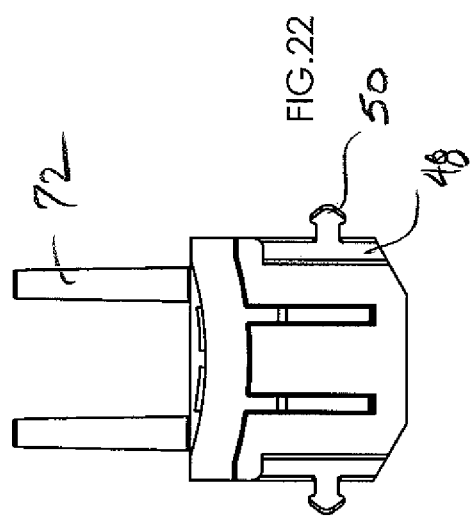

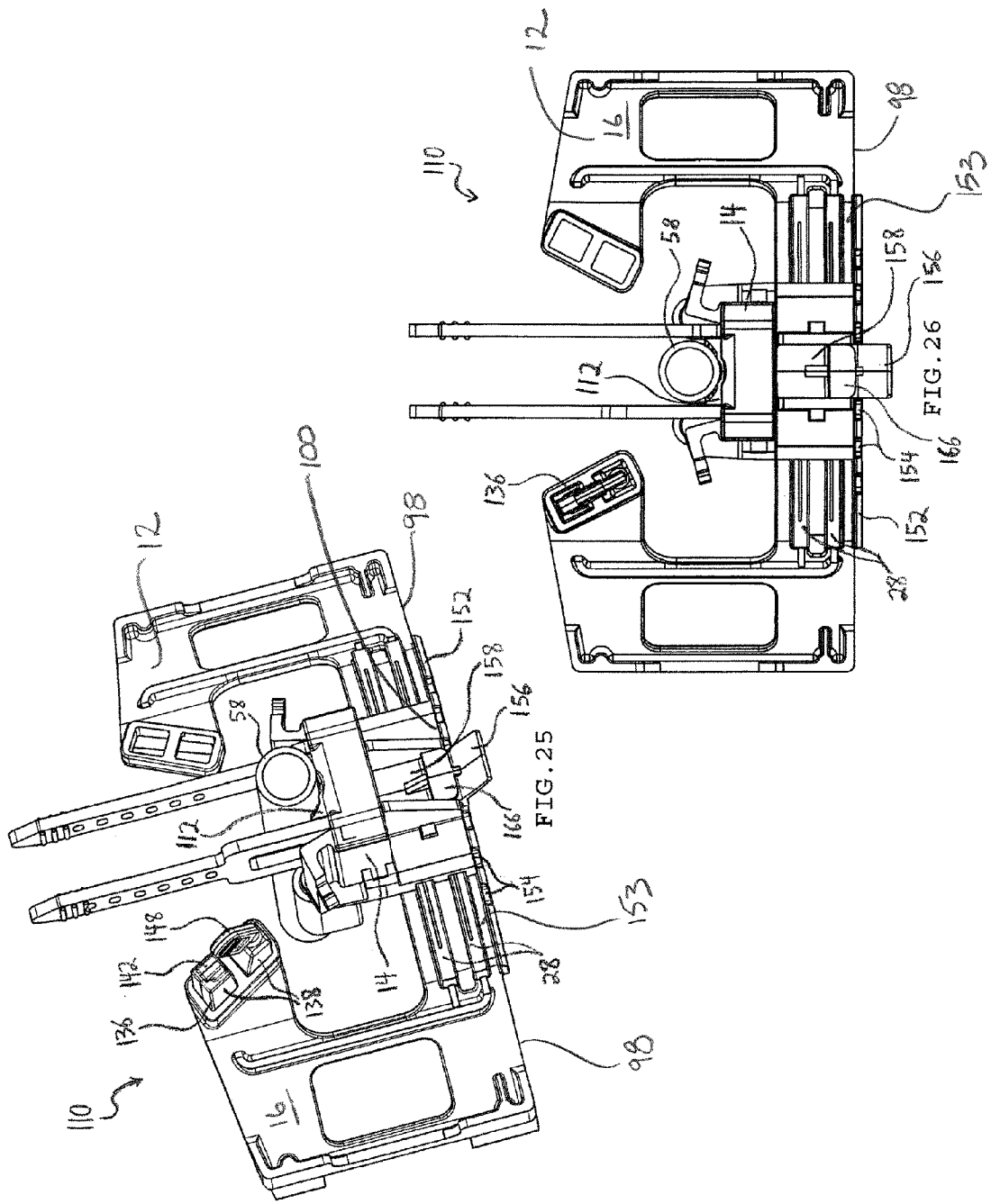

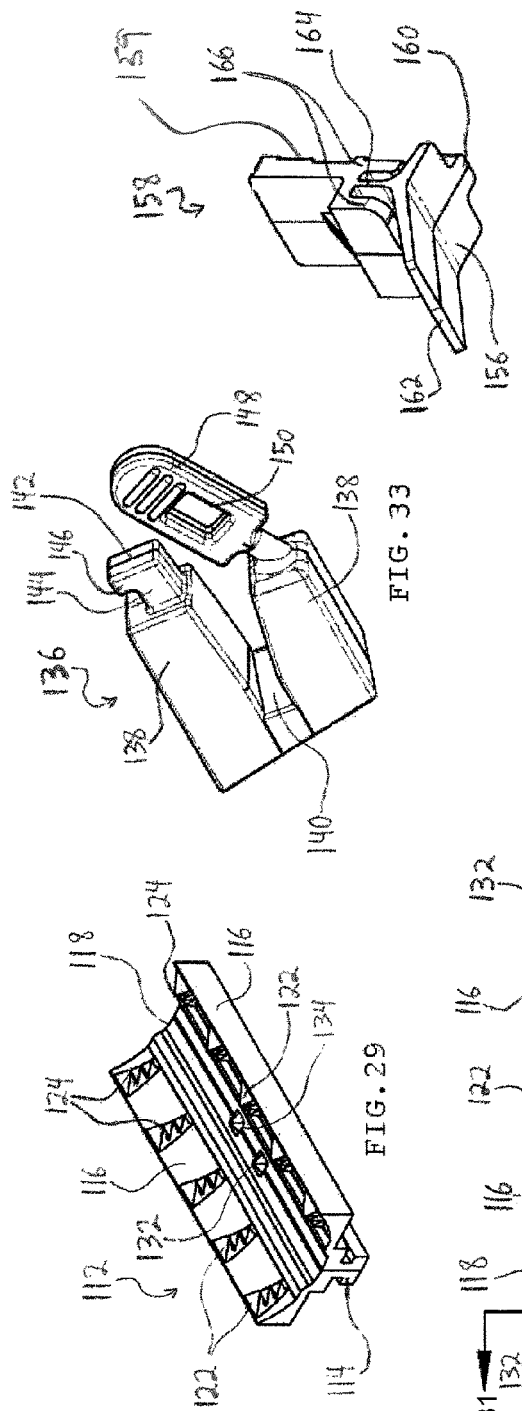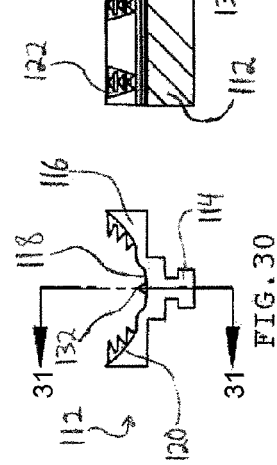

RESPIRATORY FACEMASK WITH SLIDING ENDOTRACHEAL TUBE HOLDER

RELATED APPLICATION

This application is a continuation-in-part of and claims priority under 35 U.S.C. §120 from U.S. Ser. No. 12/956,627 filed Nov. 30, 2010, now abandoned, which claimed priority under 35 U.S.C. §119(e) from U.S. Ser. No. 61/265,138 filed Nov. 30, 2009.

BACKGROUND

The present invention relates generally to an apparatus for facilitating the treatment of patients with respiratory ailments or who need breathing assistance in the course of other medical treatment, and more specifically to an improved respiratory facemask for more securely retaining an endotracheal or laryngeal tube (hereinafter "endotracheal tube") in the patient's mouth.

In conventional respiratory therapy applications, tape is often used to secure the endotracheal tube in place. The use of tape in such applications has several drawbacks. For example, tape loses adhesion when patients perspire and/or have facial hair growth, or on patients with facial burns. In addition, tape is not recommended for use on elderly patients since the tape could remove the facial skin upon tape removal.

To reduce the use of tape in such applications, facemasks have been developed which are strapped to the patient's head and provide a relatively stable platform for mounting the endotracheal tube in place. Exemplary prior art facemasks are disclosed in facemask U.S. Pat. Nos. 5,345,931 and 4,744,358, which are incorporated by reference. One drawback of the prior art products is that the endotracheal tube still became loose over time, as medical technicians perform routine monitoring and sanitation tasks in administering to the patient. As such, medical technicians still resort to the use of tape to better secure the treatment tube in place, even when a facemask is used. Another drawback is the relatively high manufacturing cost of the prior art products.

SUMMARY

The present respiratory facemask addresses drawbacks of prior art products, more securely fixes the endotracheal tube to the patient, and preferably eliminates need for tape to secure the tube in place. Structural features are provided for securing the endotracheal tube against unwanted horizontal, vertical, longitudinal, and rotational movement relative to the patient's face. In addition, a nasogastric tube is optionally secured by the present facemask. With the present side-to-side tube mount motion, oral hygiene can now be performed without the need to disassemble the device from the patient's face. Despite such lateral movement of the tube mount, the present facemask prevents unwanted vertical, longitudinal, and rotational tube movement relative to the patient's face, and maintains fixation of the endotracheal cuff location, thus preventing excessive oral secretion transfer during the period that the tube is unsecured. The transfer of excessive oral secretions below the endotracheal cuff is currently a location for the transfer of contamination, which could lead to pneumonia. Also, tracheal and laryngeal trauma is reduced.

With the present facemask, pressure upon the patient's face is more evenly distributed, lessening the possibility of pressure necrosis. Instead of hard plastic, nonporous foam rests against the patient's skin, allowing frequent facial hygiene, thus preventing bacterial growth. Another feature of the present facemask is the soft, rubber-like bite block that guards against biting, prevents tube occlusion, and inhibits patients from cutting off airflow without causing discomfort. The present facemask includes a bite block lip protector for enhanced patient comfort.

More specifically, a respiratory therapy facemask configured to be positioned against a patient's face and adjacent the patient's mouth includes a face plate configured for attachment to the patient and defining an opening, the face plate includes a laterally extending track defining a slot. A tube rest assembly is configured for being slidably engaged in the slot and for securely accommodating an endotracheal tube. The tube rest assembly is configured for directly engaging the track for lateral movement in the opening.

In another embodiment, a respiratory therapy facemask configured to be positioned against a patient's face and adjacent the patient's mouth includes a face plate configured for attachment to the patient and defining an opening, the face plate has a laterally extending track defining a slot. A tube rest assembly is configured for being slidably engaged in the slot and for securely accommodating an endotracheal tube. At least one clip is provided for engaging the tube rest assembly from a rear side of the face plate for vertically stabilizing the tube rest as it laterally slides relative to the face plate.

In yet another embodiment, a respiratory therapy facemask configured to be positioned against a patient's face and adjacent the patient's mouth includes a face plate configured for attachment to the patient and defining an opening, the face plate includes a laterally extending track defining a slot. A tube rest assembly is configured for being slidably engaged in the slot and for securely accommodating an endotracheal tube. At least one of the tube rest assembly and the face plate have ribs for facilitating the sliding engagement in the slot. A slide clip retains the tube rest assembly to the face plate and slides with the tube rest assembly in the slot, with the face plate sandwiched between the clip and the tube rest assembly. A hook clip engages the tube rest assembly and has a hook clip slidably engaging a lower edge of the opening and preventing unwanted vertical and forward movement of the tube rest assembly relative to the face plate.

Additional features of the present respiratory therapy facemask include a tube rest assembly that is configured for being slidably engaged in the slot of the track and for securely accommodating an endotracheal tube. The tube rest assembly houses a tube rest insert on which the endotracheal tube lies. Preferably, the tube rest insert is U-shaped and includes multiple teeth-like friction-enhancing formations. The U-shaped structure is configured for accommodating the shape of the endotracheal tube in a way that prevents the tube from lateral and vertical movement in the tube rest assembly when the tube is secured to the facemask. The teeth-like friction-enhancing formations on the U-shaped tube rest insert enhance the grip on the endotracheal tube, which inhibits rotational and longitudinal movement of the tube in the tube rest assembly. Tube posts are optionally provided to the insert and extend vertically through the tube rest insert for engaging the underside of the tube when it is secured to the facemask. When used in combination with the teeth-like friction enhancing formations, the tube posts provide an additional source of friction which prevents unwanted endotracheal tube movement, especially in the longitudinal direction.

Another feature of the present respiratory therapy facemask is that the face plate includes additional openings configured for accommodating clips for securing a naso-gastric (NGI) or feeding tube to the mask, preventing such tube from interfering with the medical technician's services. Each clip includes two arms that define a wedge between them and a mechanical locking mechanism that retains the NGI tube within the wedge. In a preferred embodiment, the mechanical locking mechanism features a hook at the end of one of the arms and a strap fixed to the other arm that is engageable with the hook. When the strap engages the hook, an NGI tube within the wedge is securely retained in the clip by the arms and the strap.

Still another feature of the present respiratory therapy facemask is a shelf extending along the length of the track slot. Included on the shelf is a plurality of laterally-spaced notches configured for accommodating a tab on the tube rest assembly. This feature allows the tube rest assembly to selectively fix in place at various indexed positions along the slot, which is very useful for medical technicians performing routine monitoring and sanitation tasks in administering to the patient. Using this feature, the location of the tube is optionally manipulated in a selected, indexed position without disrupting the endotracheal cuff. In addition, a latch is secured to the tube rest assembly, and includes a tab that engages the notches along the shelf for retaining the tube rest assembly in the selected, indexed position.

BRIEF DESCRIPTION OF THE DRAWINGS

FIG. 3 is a front elevation of the present facemask;

FIG. 4 is a top view of same;

FIG. 5 is a left side elevation of same;

FIG. 6 is a rear elevation of the present facemask;

FIG. 7 is a partial cross-section taken along the line 7-7 of FIG. 6 and in the direction indicated generally;

FIG. 8 is a fragmentary enlarged cross-section of FIG. 7;

FIG. 9 is a right side elevation of the present facemask tube rest assembly;

FIG. 10 is a rear elevation of the tube rest of FIG. 9;

FIG. 14 is an exploded top perspective view of the present tube rest and pad;

FIG. 14A is an assembled top perspective view of the present tube rest and pad;

FIG. 15 is a front bottom perspective view of the present hook clip;

FIG. 15A is a rear bottom perspective view of the present hook clip of FIG. 15;

FIG. 16 is a rear perspective view of the present slide clip;

FIG. 16A is a front perspective view of the slide clip of FIG. 16;

FIG. 17 is a front elevation of the present facemask face plate;

FIG. 18 is a right side view of the face plate shown in FIG. 17;

FIG. 19 is a cross-section taken along the line 19-19 in FIG. 17 in the direction indicated generally;

FIG. 20 is a fragmentary top rear perspective view of the present tube rest assembly;

FIG. 21 is a rear elevation of the tube rest assembly shown in FIG. 20;

FIG. 22 is a fragmentary overhead plan view of the tube rest assembly shown in FIG. 20;

FIG. 25 is a lower front perspective view of another embodiment of the present respiratory facemask;

FIG. 26 is a front elevation of the facemask of FIG. 25;

FIG. 29 is an assembled top perspective view showing an alternative embodiment of a tube rest insert and tube post grips;

FIG. 30 is a front elevation view of the tube rest insert of FIG. 29;

FIG. 31 is a cross-section taken along the line 31-31 of FIG. 30 and in the direction indicated generally;

FIG. 32 is a top perspective view of the tube post grips;

FIG. 33 is a perspective view of an alternate embodiment of a clip with a locking mechanism for securing a naso-gastric tube to the present facemask;

FIG. 34 is a lower front perspective view of the present latch for fixing the tube rest assembly at various indexed lateral positions along the track; and FIG. 35 is a lower rear perspective view of the present latch.

DETAILED DESCRIPTION

Figure 1:
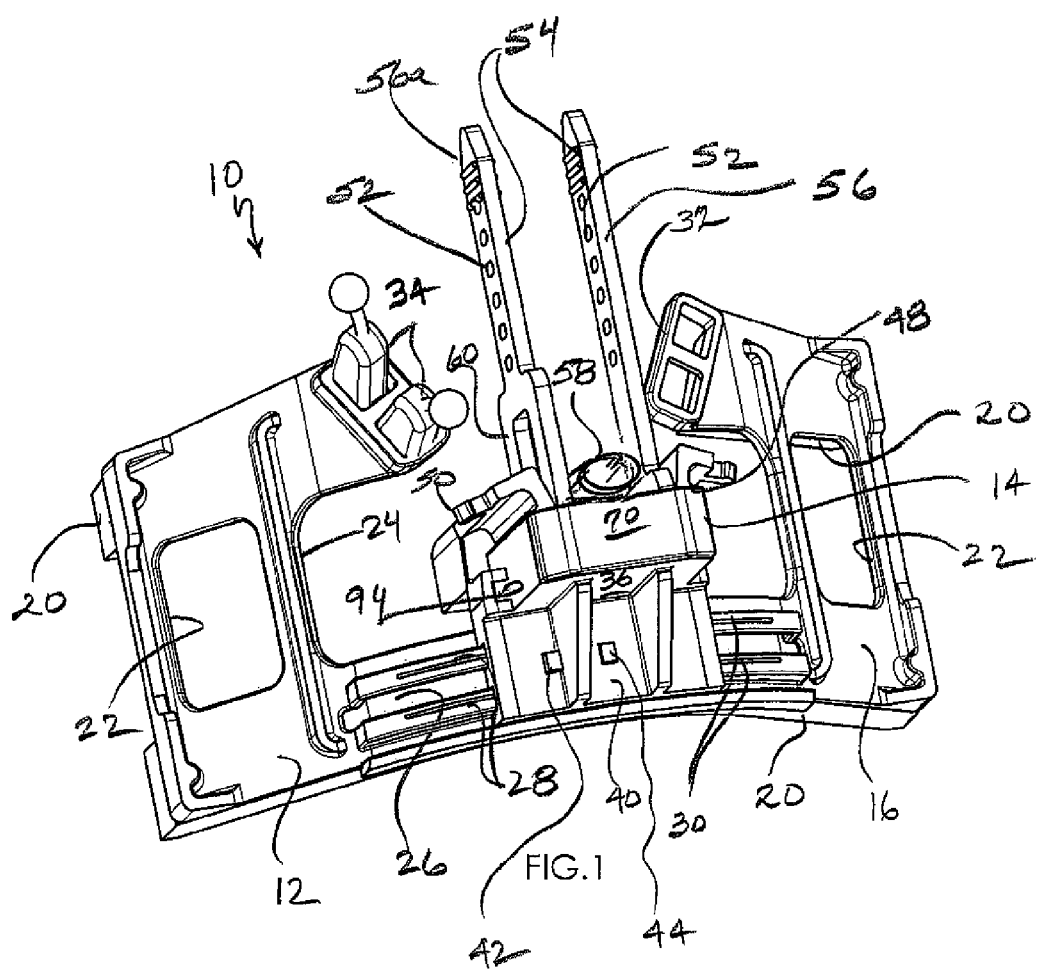
FIG. 1 is a lower front perspective view of the present respiratory facemask.

Referring now to FIGS. 1-7, the present facemask, generally designated 10, includes a face plate 12 configured for being secured to the face of a patient by a harness (not shown) as is well known in the art and described in U.S. Pat. Nos. 5,345,931 and 4,744,358 incorporated by reference. The main purpose of the present facemask 10 is to secure an endotracheal or laryngeal tube (hereinafter "endotracheal tube") in place in the patient's mouth, the tube being separate from the facemask 10. A main feature of the present facemask 10 is that the endotracheal tube is actually secured to a tube rest assembly 14, which directly contacts and is laterally slidable relative to the face plate 12 to permit the performance of oral hygiene operations on the patient while the tube is maintained in the patient's trachea and mouth for therapeutic concerns. It is contemplated that both the face plate 12 and the tube rest assembly 14 are made of generally rigid, self-supporting plastic materials as are known in the art, including, but not limited to polyvinylchloride (PVC).

The face plate 12 includes a front surface 16 and a rear surface 18, the latter designed to contact the patient's face and as such is provided with at least one pad 20 made of relatively soft material such as polyurethane foam or the like to facilitate patient comfort. In the preferred embodiment, the patient's cheeks and chin surface are contacted by the rear surface 18, which is covered by the pads 20, numbering three. However, the number, placement and composition of the pads 20 may vary to suit the application. Also, the face plate 12 is provided with at least one and preferably a pair of openings 22 for attaching the harness (not shown) used to secure the facemask 10 to the patient's head, as is known in the art.

Between the openings 22 is a preferably central opening 24 which defines a space for lateral movement of the tube rest assembly 14. Below the central opening 24 is a generally horizontally or laterally extending slot 26 defined on upper and lower ends by a track 28, preferably integrally joined to the face plate 12. Referring now to the front surface 16 of the face plate 12, the track 28 is provided with outwardly projecting ribs 30 which facilitate lateral sliding of the tube rest assembly 14 as will be described below. Above the track 28, an upper border of the central opening 24 is provided with a pair of clip mounts 32 configured for accommodating clips 34 in a friction-fit engagement for securing a naso-gastral intestinal (NGI) tube (not shown). The NGI tube, which is distinct from the main, endotracheal tube, is basically jammed into a wedge-like foam-lined portion of the clip 34 and held by a friction fit.

Referring now to FIGS. 1, 2, 7, 8, 16 and 16A, the tube rest assembly 14 includes a forwardly located tube rest assembly body 36 and a relatively rearwardly located bite block 38 connected to the tube rest assembly body, preferably by having a portion being integrally molded, however assembly of various components by chemical adhesive, ultrasonic molding or fasteners is also contemplated. In the context of the present facemask 10, "forwardly" refers to away from a patient's face, and "rearwardly" refers to toward the patient's face.

An important feature of the present facemask 10 is that the tube rest assembly 14 is slidably secured to the face plate 12 at several locations along or adjacent a vertical axis defined by points of engagement of the two components. When viewed from the front surface 16, the tube rest assembly body 36 preferably includes a front panel 40 having at least one opening 42 for accommodating optionally barbed prongs 44 secured to a slide clip 46 slidingly engaged on the rear surface 18 on the track 28. The number and placement of the prongs 44 may vary to suit the situation, and in one embodiment, there are preferably three prongs 44 received in corresponding openings 42 in the front panel 40. The engagement of the prongs 44 in the openings 42 secures the tube rest assembly 14 to the face plate 12 for lateral sliding motion facilitated by the engagement of an inner surface 47 (FIG. 9) of the front panel 40 with the ribs 30. It is contemplated that the prongs 44 have hook or barb-shaped ends (FIG. 16) for enhancing the engagement between the slide clip 46 and the tube rest assembly 14, preventing unwanted vertical movement of the tube rest assembly relative to the face plate 12. In addition, the front panel has at least one rearwardly projecting tab 41 (FIG. 20) that matingly engages holes 43 (FIG. 16) in the slide clip 46.

Figure 2:
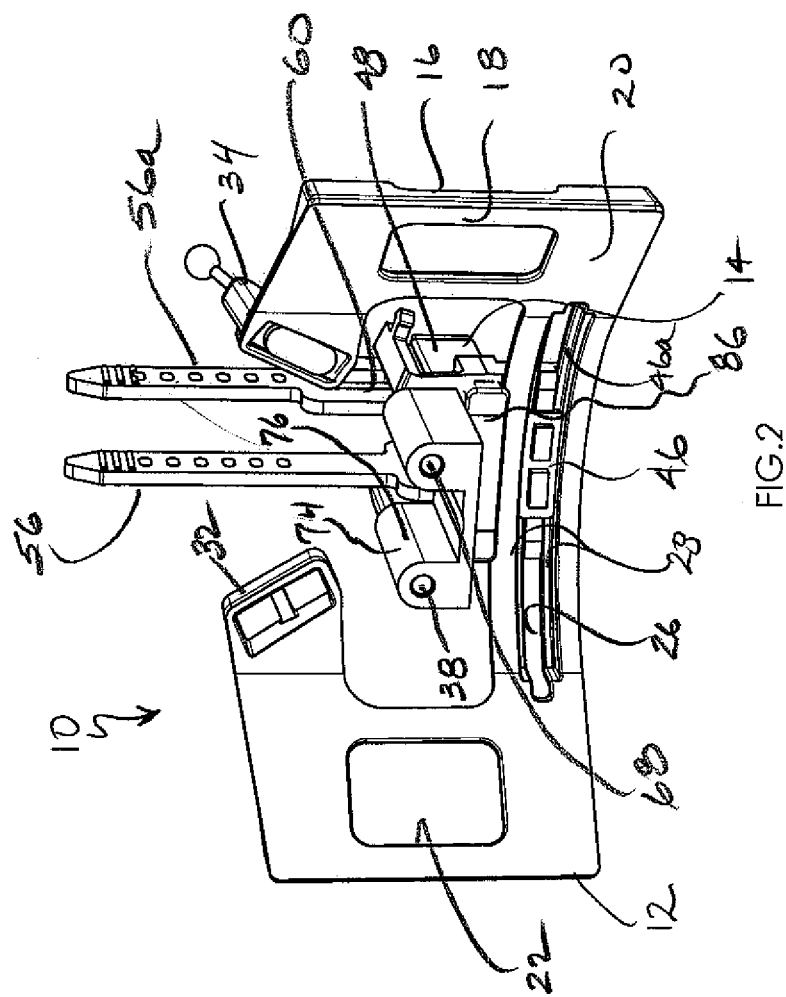
FIG. 2 is an upper rear perspective view of the facemask of FIG. 1 without the pads.

As also seen in FIG. 16, the slide clip 46 also has elongated ribs 46a for facilitating this lateral sliding action. As seen in FIGS. 2 and 6, the slide clip 46 slides behind the pad 20 when viewed from the rear surface 18, or forward of the patient, so that the patient's skin is not exposed to the sliding movement. It is contemplated that the ribs 46a may alternatively be placed on the rear surface 18 of the face plate 12 near the track 28 and adjacent the slot 26 (FIG. 2)

Figure 13:
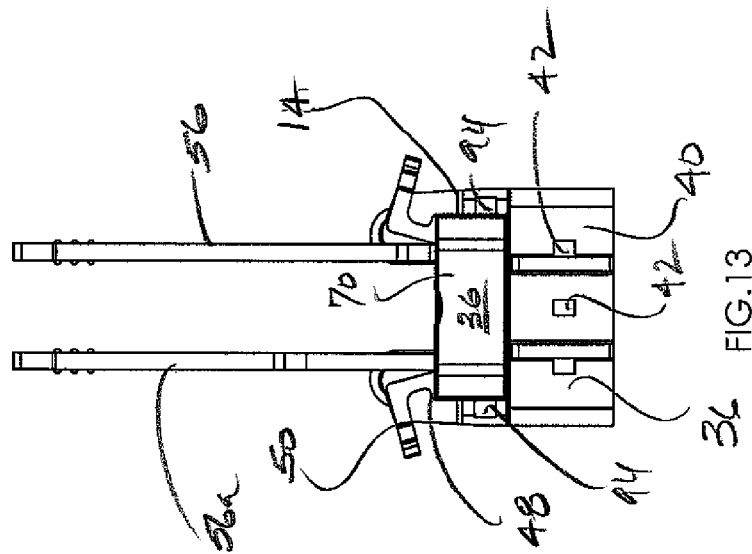
FIG. 13 is a fragmentary front elevation of the present tube rest assembly.
Figure 12:
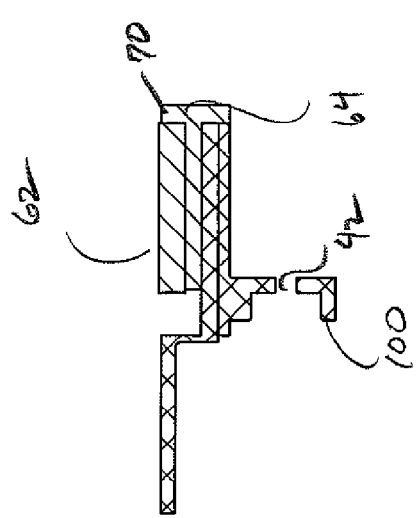
FIG. 12 is a section taken along the line 12-12 of FIG. 10 and in the direction indicated generally.
Figure 11:
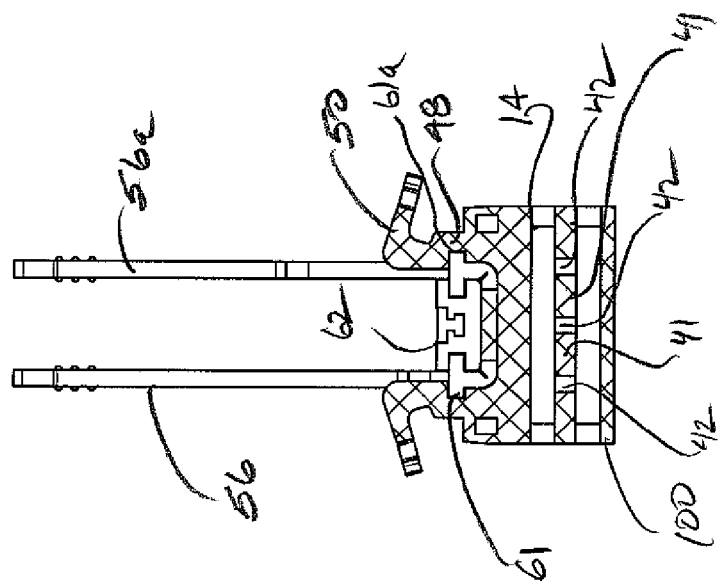
FIG. 11 is a cross-section taken along the line 11-11 of FIG. 9 and in the direction indicated generally.
Figure 23:
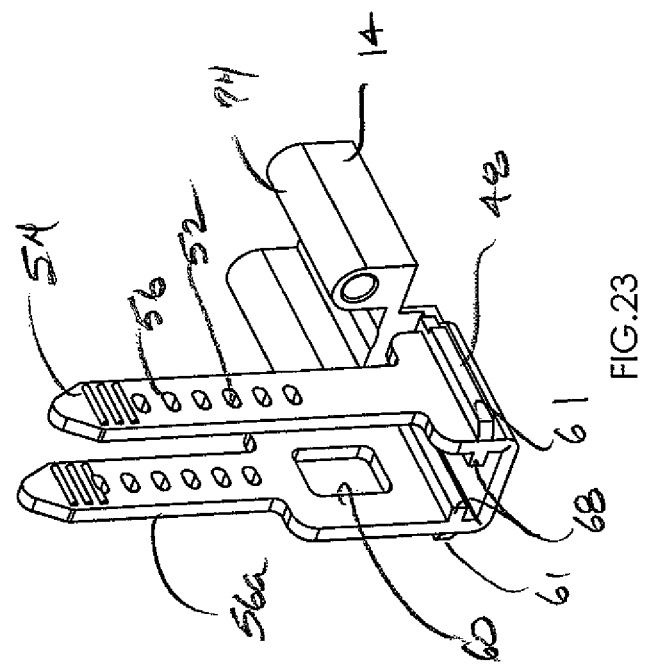
FIG. 23 is a top perspective view of the present strap and bite block.
Figure 24:
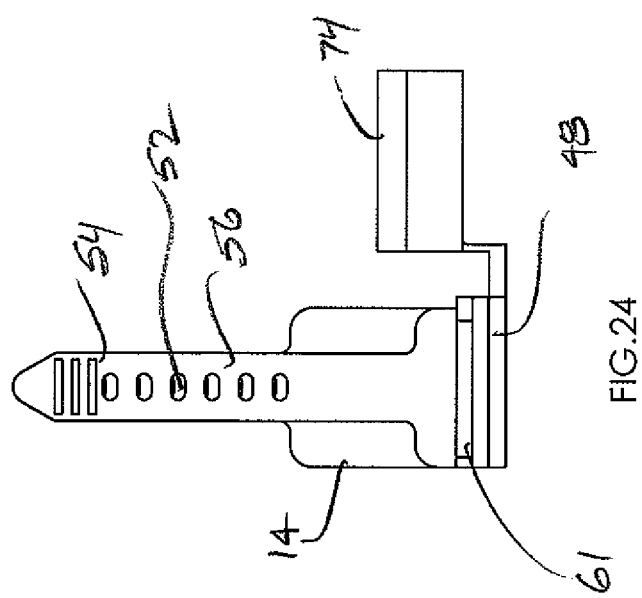
FIG. 24 is a right side elevation of the strap and bite block shown in FIG. 23.
Figure 27:
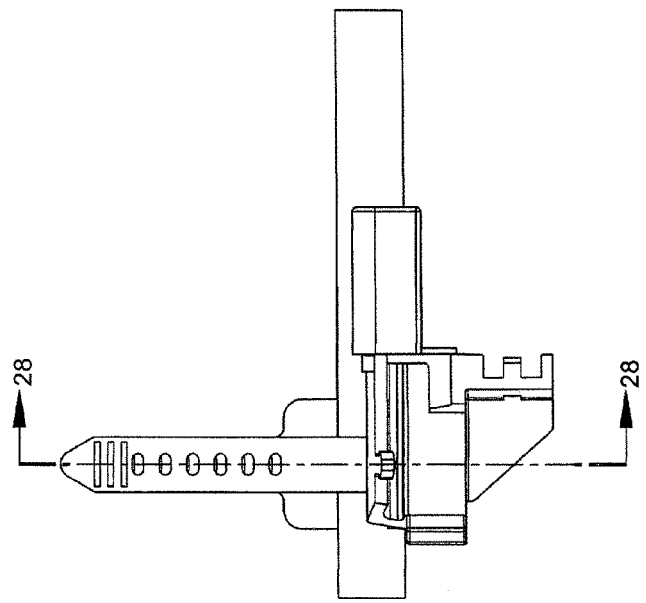
FIG. 27 is a right side elevation of the tube rest assembly of the facemask of FIG. 25.

Secured to an upper margin of the front panel 40 is a forwardly projecting tube holder 48 having a generally "U"-shape when viewed from the front. At least one leg of the U includes an angled, arrow-shaped strap anchor 50. Each anchor 50 is constructed and arranged to engage a desired one of a series of linearly spaced locking apertures 52 on each end 54 of an endotracheal locking strap 56 (FIGS. 23 and 24). The two ends 54 overlap each other to secure an endotracheal tube 58 (FIG. 1) in place. One strap 56a includes an opening 60 for receiving the other strap 56 in this overlapping manner. As seen in FIGS. 11, 13 and 23, the straps 56, 56a are preferably fastened to the tube holder 48 by engagement between laterally extending ribs 61 with corresponding grooves 61a on the tube holder 48 (FIGS. 20 and 21).

Referring now to FIGS. 11, 12, 14 and 14A, the endotracheal tube 58 rests upon a relatively soft tube rest insert 62 made of rubber-like or low Durometer resilient polyvinyl chloride (PVC) material. Since the endotracheal tube 58 is also typically made of PVC, the inherent self-adhesive nature of PVC enhances the adhesion of the tube to the tube rest insert, and more securely retains the tube in position. In one embodiment, the tube rest insert 62 has a generally uneven "I-beam" construction when viewed in cross-section and is held in place on a relatively rigid or higher Durometer tube rest 64 by a tongue-in-groove relationship best seen in FIG. 14. Once slidably installed in the relatively hard plastic tube rest 64, the tube rest insert 62 of this embodiment is generally flush with the tube rest 64.

The tube rest 64 is in turn slidably engaged into the tube holder 48 by a tongue-in-groove arrangement defined by lateral grooves 66 in the pad which slidingly engage horizontal ribs 68 in the tube holder 48 (FIG. 23). As seen in FIGS. 13 and 14, the tube rest 64 has a front panel 70. Thus, when the endotracheal tube 58 is placed upon the tube rest insert 62, the tube is secured in part by this self-adhesion and in part by the endotracheal locking straps 56.

Referring to FIGS. 2, 6 and 20-24, rearwardly projecting from the tube holder 48 are a pair of parallel, spaced rods 72 upon which are matingly engaged a bite block pad 74. The bite block pad 74 is also generally "U"-shaped when viewed from the rear (FIG. 10) and is made of a generally soft, rubber-like, PVC plastic material to be comfortably inserted into the patient's mouth during respiratory therapy, which refers to any type of medical treatment, including but not limited to emergency, first responder, paramedic use, and anesthesia. The pad 74 is friction fit upon the rods 72, and may be secured if desired using chemical adhesive or the like. In addition, the pad 74 defines a rest 76 for receiving the endotracheal tube 58.

Referring now to FIGS. 2, 7, 8, 15 and 15A, the tube rest assembly 14 is also more securely and slidably held to the face plate 12 by at least one hook clip 78. The hook clip 78 is disposed near a lower edge 80 of the central opening 24 and closer to the tube holder than the track 28. At least one and preferably a pair of lugs 82, optionally provided with barbs 84 are connected to a main panel 86. A lower edge 88 of the main panel is provided with a hook rib 90 that slidably engages an undercut 92 on the rear surface. The lugs 82 matingly engage openings 94 in the tube rest assembly 14 (FIGS. 11, 13 and 20).

The use of the hook clip 78 supplements the slide clip 46 and helps prevent unwanted forward or vertical movement of the tube rest assembly 14 relative to the face plate 12 during respiratory therapy, or during oral hygiene conducted by a medical technician, at which time the tube rest assembly 14 is laterally moved along the track 28 as needed. Due to the support provided by the hook clip 78, a relatively stable engagement of the endotracheal tube in the patient's mouth is maintained during the lateral sliding movement of the tube rest assembly 14.

In addition, referring now to FIGS. 1 and 17-19, the face plate 12 is preferably provided with a shelf 96 projecting forwardly from a lower edge 98 of the face plate and past the front surface 16. The shelf 96 thus defines a groove for slidingly engaging a lower edge 100 of the tube rest assembly (FIGS. 8, 11, 12, 20) for still further preventing unwanted vertical movement and thus vertically stabilizing the tube rest assembly 14 relative to the face plate 12. It will be appreciated that the dimensions of the shelf 96 may vary to suit the application.

From the above description, it will be seen that the present respiratory facemask 10 provides smooth relative sliding motion of the tube rest assembly 14 relative to the face plate 12. The multiple points of slidable attachment, at the slide clip 46, the hook clip 78, the shelf 96 and the tabs 41 provide vertical sliding stability to the tube rest assembly 14, preventing unwanted forward or vertical movement. It is preferred that the components are manufactured to close tolerances, preferably approximately 0.002 inch to prevent undue play between components.

Referring now to FIGS. 25-26, an additional embodiment of the present respiratory facemask is generally designated 110. Components shared with the facemask 10 are designated with identical reference numbers. Features included on the facemask 110 include an enhanced gripping surface for the endotracheal tube 58, indexed movement of the tube rest assembly 14 relative to the face plate 12, a pivoting latch for retaining the tube rest assembly in a selected indexed position, and a hook and strap assembly for more positively securing the NGI tube in place.

Figure 28:
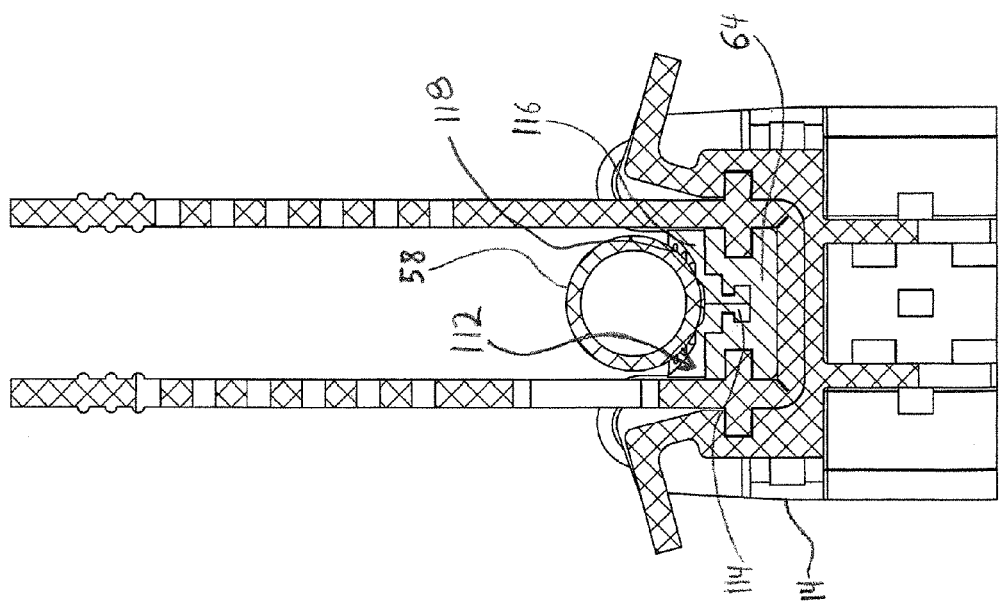
FIG. 28 is a cross-section taken along the line 28-28 of FIG. 27 and in the direction indicated generally.

Referring now to FIGS. 28-31, an alternate tube rest insert, generally designated 112, is provided with a lower or depending portion 114 located between a pair of sloping walls 116. The sloping walls 116 are generally symmetrical when viewed in cross-section from the front (FIG. 30), and are sloped such that the vertical height of each wall increases with distance from a central vertical axis of the tube rest insert 112 when viewed from the front. Thus, the sloping walls 116 define a generally U-shaped track 118 for accommodating the endotracheal tube 58 as shown in FIG. 28, which prevents tube movement in the lateral and vertical directions relative to the tube rest assembly 14. The sloped or U-shape of the tube rest insert 112 also increases the amount of contact surface area between the tube 58 and the insert, which increases friction on the tube, severely restricting rotational and longitudinal tube movement.

As shown in FIGS. 28 and 30, the lower portion 114 resembles an uneven I-beam when viewed in cross-section from the front, which allows the tube rest insert 112 to be slidably engaged and held in place on the tube rest 64 by a tongue-in-groove relationship with a complementary formation on the tube rest. The tube rest insert 112 is preferably constructed of a rigid material, such as a high Durometer hard plastic, for example polycarbonate or equivalent materials.

As shown in FIGS. 29-31, the tube rest insert 112 has at least one friction-enhanced formation 120 along the generally U-shaped track 118. In a preferred embodiment, the friction-enhanced formation 120 is a set of ridges 122 extending transversely relative to a longitudinal axis of the insert 112 and being longitudinally spaced along the wall 116. Referring now to FIG. 29, each ridge 122 includes angled projections 124 that culminate in a point and have the appearance of shark teeth. The rigid material of the tube rest insert 112 and the teeth-like ridges 122 allow the endotracheal tube 58 to be strapped tightly to the tube rest assembly 14 and enhance the grip on the tube, preventing the tube from unwanted rotational, vertical, lateral, and longitudinal movement relative to the tube rest assembly 14, which is an important function of the present facemask 110.

Referring now to FIGS. 29, 31 and 32, optional tube post grips 126 include a base 128 and at least one post 130 extending perpendicularly from the plane of the base 128. An apex 132 of each post 130 preferably ends in a point, but other embodiments have rounded or even relatively flat apexes. Tube post grips 126 are preferably made of plastic, such as rubber or PVC. As shown in FIGS. 29-31, each post 130 of the tube post grips 126 preferably extends through an opening 134 in the tube rest insert 112, such that each apex 132 extends into the defined U-shaped track 118. In a preferred embodiment shown in FIGS. 29 and 30, each post 130 extends vertically through the tube rest insert 112 along the longitudinal axis, however the orientation and location of the posts relative to the tube rest insert may be modified. The tube posts 130 enhance a grip on the endotracheal tube 58 by providing another frictional surface that contacts the tube 58, restricting undesired tube movement, especially longitudinally along the tube rest insert 112, when the tube is strapped to the tube rest assembly 14.

Referring now to FIGS. 25 and 33, another feature of the present respiratory facemask 110 is an alternate form of clips, generally designated 136, insertable through the clip mounts 32 and used to secure a second tube, such as an NGI tube or a feeding tube (not shown) to the facemask. The clips 136 have a pair of arms 138 which are joined at one end to define a wedge 140 between them that accommodates an NGI tube by friction fit. In addition, to more securely retain the NGI tube within the wedge 140, the clips 136 include a mechanical locking mechanism. As shown in FIG. 33, one arm 138 of each clip 136 features a fastener 142, which is preferably a generally axially-extending projection 144 with an optional hook end 146. The other arm 138 of the clip 136 is provided with an attached retaining strap 148. The retaining strap 148 is preferably made of a resilient material such as rubber, a low Durometer resilient plastic, or a textile, among other materials with equivalent properties. The retaining strap 148 preferably includes an aperture 150 for being mechanically fitted over the fastener 142, such that the fastener extends through the aperture. Once the retaining strap 148 is fitted on the fastener 142, an NGI tube extending through the wedge 140 of the clip 136 will be surrounded on all directions and thus secured within the clip.

Referring now to FIGS. 25, 26, 34 and 35, the face plate 12 is preferably provided with a shelf, generally designated 152, which projects forwardly from a lower edge 98 of the face plate and past the front surface 16. The shelf 152 defines a groove 153 for slidably engaging the lower edge 100 of the tube rest assembly 14 for further preventing unwanted vertical movement and thus vertically stabilizing the tube rest assembly relative to the face plate 12.

As shown in FIGS. 25 and 26, the shelf 152 further defines a plurality of laterally-spaced, forwardly projecting notches 154 when viewing the facemask 110 vertically from the front. Each notch 154 is designed to be individually engageable by a releasable, biased tab 156 on the tube rest assembly 14. Once the releasable tab 156 engages a notch 154 as is described in greater detail below, the tube rest assembly 14 is fixed in place, unable to slide laterally along the track 28 until the tab is released. In use, the selective engagement provided by the defined notches 154 and the releasable tab 156 allow the tube rest assembly 14 to be selectively locked in place at various indexed, user selected positions along the length of the track 28. This feature enhances the ability of medical technicians to provide oral hygiene services to the patient wearing the facemask 110, without removing the mask and potentially disrupting the endotracheal cuff.

Referring now to FIGS. 34 and 35, the releasable tab 156 is part of a latch 158 used for holding the tube rest assembly 14 in the selected position. In a preferred embodiment, the latch 158 is attached to the tube rest assembly 14 at a surface 159, preferably by solvent welding (glue) or by molding the latch 158 integrally with the tube rest assembly 14 as one piece. It is contemplated that the latch 158 is made of the same or a similar, generally rigid, self-supporting plastic material as both the face plate 12 and the tube rest assembly 14, such as PVC or the like.

As shown in FIG. 34, the 156 includes a lug-like projection 160 for engaging the notches 154 along the shelf 152, and a handle portion 162 for facilitating user manipulation of the tab 156 to open or release the latch 158. In addition, the tab 156 is connected to the latch 158 by a living hinge 164 which allows the tab 156 to pivot along the axis of the hinge. To prevent the tab 156 from over-extending, which could damage the hinge 164, the latch 158 includes barriers 166 on each side of the living hinge which restrain the pivoting movement within a pre-defined range. It is possible to use only one such barrier 166 for the same effect, especially on the side of the hinge 164 facing away from the shelf 152, since motion of the tab 156 in the direction of the shelf will already be restrained by the shelf itself. Due to the construction of the living hinge 164, the tab 156 is biased toward an engaged position where the projection 160 is urged into engagement with a selected notch 154. User manipulation of the handle portion 162 pivots the tab 156 about the hinge 164 to release the engagement and allow a user to laterally adjust the position of the tube rest assembly 14 relative to the face plate 12.

While particular embodiments of the present respiratory facemask with sliding endotracheal tube holder have been shown and described, it will be appreciated by those skilled in the art that changes and modifications may be made thereto without departing from the invention in its broader aspects and as set forth in the following claims.

What is claimed:

1. A respiratory therapy facemask configured to be positioned against a patient's face and adjacent the patients mouth, comprising:
   a face plate configured for attachment to the patient and defining an opening, said face plate including a laterally extending track defining a slot; and
   a tube rest assembly including a depending front panel configured for engaging a slide clip slidably associated with said track on a rear surface of said face plate, wherein said slide clip has at least one prong matingly engaging an associated opening in said depending front panel;
   said tube rest assembly is configured for being slidably engaged in said slot and for securely accommodating an endotracheal tube, said tube rest assembly being configured for directly engaging said track for lateral movement in said opening; and
   said track is provided with at least one rib extending from an outer surface of said track and forming a contact plane for facilitating sliding action of said tube rest assembly relative to said face plate, said contact plane being formed by only a portion of said at least one rib.

2. The facemask of claim 1 wherein said depending front panel has a rear surface that engages said track and slidably engages said contact plane of said at least one rib.

3. The facemask of claim 1 wherein said at least one prong is barbed.

4. The facemask of claim 1 wherein said face plate has a rear surface and said track includes at least one rib projecting from said rear surface for facilitating sliding action of said slide clip in said slot.

5. The facemask of claim 1 wherein said tube rest assembly includes a tube holder configured for receiving the endotracheal tube, said tube holder provided with at least one resilient pad upon which the tube is disposable.

6. The facemask of claim 5 wherein said at least one resilient pad is comprised of a softer material than a plastic tube rest, said resilient pad is slidably engaged in said plastic tube rest.

7. The facemask of claim 1 wherein said tube rest assembly includes a tube holder, said tube holder provided with at least one rigid insert disposable.

8. The facemask of claim 7 wherein said at least one rigid insert includes sloping walls defining a generally U-shaped track when viewed in vertical cross-section and a friction-enhanced formation along said sloping walls.

9. The facemask of claim 8 wherein said friction-enhanced formation includes at least one set of teeth.

10. The facemask of claim 7 wherein said tube holder includes at least one post with a pointed apex extending through the at least one rigid insert such that only the pointed apex of the post extends beyond a thickness of the at least one rigid insert.

11. The facemask of claim 1 wherein said tube rest assembly is provided with a pair of locking straps configured to overlappingly engage each other for securing the endotracheal tube in place.

12. The facemask of claim 1 wherein said tube rest assembly includes a tube holder provided with at least one rearwardly projecting rod, and at least one bite block pad associated with each said rod.

13. The facemask of claim 1 wherein said opening is dimensioned for accommodating lateral sliding action of said tube rest assembly, and said tube rest assembly is slidably secured to said face plate by at least one hook clip slidably engaging an edge of said face plate defining said opening, said at least one hook clip being constructed and arranged for overhanging said edge for preventing unwanted forward or vertical movement of said tube rest assembly relative to said face plate.

14. The facemask of claim 13 wherein said edge is located above said track.

15. The facemask of claim 1 wherein said face plate has a rear surface configured for contacting the patient's face, and being provided with at least one resilient pad.

16. The facemask of claim 1 further including at least one clip mount configured for accommodating a respective tube clip constructed and arranged for receiving and securing a second tube by a friction fit in a wedge-shaped portion.

17. The facemask of claim 1 further including at least one tube clip with two arms defining a wedge-shaped portion for receiving a second tube wherein one of the two arms has a fastener and the other arm has a retaining strap such that said retaining strap engages said fastener.

18. The facemask of claim 17 wherein said fastener has a hook and said retaining strap includes an aperture such that fitting said aperture of said retaining strap around said hook secures the second tube by a mechanical fit within said wedge-shaped portion.

19. A respiratory therapy facemask configured to be positioned against a patient's face and adjacent the patient's mouth, comprising:
   a face plate configured for attachment to the patient and defining an opening, said face plate including a laterally extending track defining a slot;
   a tube rest assembly configured for being slidably engaged in said slot and for securely accommodating an endotracheal tube;
   a shelf projecting from a lower edge of said face plate past a front surface for vertically stabilizing said tube rest assembly, wherein said shelf defines a plurality of forward-oriented laterally-spaced notches which are individually engageable by a releasable tab on said tube rest assembly such that said tube rest assembly can be fixed at various lateral positions along said slot; and
   at least one clip provided with one or more barbed prongs for matingly engaging said tube rest assembly from a rear side of said face plate for preventing axial rotation of the tube rest within said track and for vertically stabilizing the tube rest as it laterally slides relative to said face plate.

20. The facemask of claim 19, wherein said plurality of laterally-spaced notches is individually engageable by said releasable tab on a latch secured to said tube rest assembly.

21. The facemask of claim 20, wherein said latch contains a living hinge and at least one barrier to restrain pivot movement.

22. The facemask of claim 19 further including a slide clip retaining said tube rest assembly to said face plate and sliding with said tube rest assembly in said slot, with said face plate sandwiched between said slide clip and said tube rest assembly; and a hook clip engaging said tube rest assembly and having a hook rib slidably engaging a lower edge of said opening and preventing unwanted vertical and forward movement of said tube rest assembly relative to said face plate.

23. The facemask of claim 22, wherein at least one of said slide clip and said hook clip matingly engage said tube rest assembly, said at least one slide clip matingly engaging said tube rest assembly through at least one barbed prong, and said at least one hook clip matingly engaging said tube rest assembly through at least one barbed lug.

24. A respiratory therapy facemask configured to be positioned against a patient's face and adjacent the patients mouth, comprising:

a face plate configured for attachment to the patient and defining an opening, said face plate including a laterally extending track defining a slot;

a tube rest assembly configured for being slidably engaged in said slot and for securely accommodating an endotracheal tube upon a resilient pad which is slidably inserted into the tube rest assembly via an interlocking tongue-in-groove arrangement, at least one of said tube rest assembly and said face plate having ribs for facilitating the sliding engagement in said slot;

a slide clip engaging said tube rest assembly through at least one barbed prong and retaining said tube rest assembly to said face plate and sliding with said tube rest assembly in said slot, with said face plate sandwiched between said clip and said tube rest assembly; and a hook clip engaging said tube rest assembly through at least one barbed lug and having a hook rib slidably engaging a lower edge of said opening and preventing unwanted vertical and forward movement of said tube rest assembly relative to said face plate.

* * * * *